United States Patent
Dominici et al.

(10) Patent No.: US 10,273,457 B2
(45) Date of Patent: Apr. 30, 2019

(54) METHOD OF OBTAINING A POPULATION OF CELLS

(71) Applicants: Massimo Dominici, Ferrara (IT); Luigi Cafarelli, Modena (IT); Elena Veronesi, Finale Emilia (IT); Maria Serena Piccinno, Modena (IT); Paolo Paolucci, Bologna (IT); Giorgio De Santis, Modena (IT); Pierfranco Conte, Pisa (IT)

(72) Inventors: Massimo Dominici, Ferrara (IT); Luigi Cafarelli, Modena (IT); Elena Veronesi, Finale Emilia (IT); Maria Serena Piccinno, Modena (IT); Paolo Paolucci, Bologna (IT); Giorgio De Santis, Modena (IT); Pierfranco Conte, Pisa (IT)

( * ) Notice: Subject to any disclaimer, the term of this patent is extended or adjusted under 35 U.S.C. 154(b) by 861 days.

(21) Appl. No.: 14/309,086

(22) Filed: Jun. 19, 2014

(65) Prior Publication Data
US 2014/0302605 A1    Oct. 9, 2014

Related U.S. Application Data

(63) Continuation-in-part of application No. 13/641,117, filed as application No. PCT/IB2011/051614 on Apr. 14, 2011, now abandoned.

(30) Foreign Application Priority Data

Apr. 14, 2010   (IT) .............................. MO2010A0111

(51) Int. Cl.
*C12N 5/0775*    (2010.01)

(52) U.S. Cl.
CPC ........ *C12N 5/0667* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 2005/0076396 A1* | 4/2005 | Katz | C12N 5/0068 800/8 |
| 2007/0238175 A1* | 10/2007 | Chi | C12N 5/0679 435/378 |
| 2007/0264239 A1* | 11/2007 | Huard | C12N 5/0657 424/93.7 |
| 2007/0274960 A1* | 11/2007 | Harman | C12N 5/0667 424/93.7 |
| 2007/0274965 A1* | 11/2007 | Mitchell, II | C12N 5/0647 424/93.7 |
| 2010/0304477 A1* | 12/2010 | Buscher | C12N 5/0667 435/325 |
| 2013/0130381 A1* | 5/2013 | Dominici | C12N 5/0667 435/381 |

FOREIGN PATENT DOCUMENTS

WO      WO 03080801 A2 * 10/2003 ........... C12N 5/0067

OTHER PUBLICATIONS

Sigma-Aldrich www. safcglobal.com/etc/medialib/docs/Sigma/Formulation/m0894for.Par.0001.File.tmp/m0894for.pdf, and http://www.sigmaaldrich.com/life-science/cell-culture/learning-center/media-formulations/dme.html.*
Sun et al., Ambient fine particulate matter and ozone exposures induce inflammation in epicardial and perirenal adipose tissues in rats fed a high fructose diet, Particle and Fibre Toxicology, 2013, vol. 10, pp. 1-20.*
Collagenase Worthington Enzyme Manual http://web.archive.org/web/20090506055141/http://www.worthington-biochem.com/CLS/default.html.*
Weisberg et al., Obesity is associated with macrophage accumulation in adipose tissue, The journal of Clinical Investigation, 2003, vol. 112, pp. 1796-1808.*
Belly Dancer orbital shaker, Sigma catalog, accessed Aug. 28, 2017 at: http://www.sigmaaldrich.com/catalog/product/sigma/z768529?lang=en&region=US.*
Dubois, Severine G., et al. "Isolation of human adipose-derived stem cells from biopsies and liposuction specimens." Mesenchymal Stem Cells. Humana Press, 2008. 69-79. (Year: 2008).*

* cited by examiner

*Primary Examiner* — Robert J Yamasaki
(74) *Attorney, Agent, or Firm* — Themis Law

(57) ABSTRACT

A method of obtaining stromal progenitor cells (SPC) from subcutaneous adipose tissue by incubation of a very small volume of the subcutaneous adipose tissue in an enzyme solution produces SPC that are usable in medical applications based on autologous SPC even on individuals having a body mass index lower than 18.5.

12 Claims, 5 Drawing Sheets

OIL RED O

CONTROLS          DIFFERENTIATED

METHOD OF OBTAINING A POPULATION OF CELLS

FIELD OF THE INVENTION

The present invention relates to a method of obtaining a population of cells, particularly a population of stromal progenitor cells from a quantity of white adipose tissue collected from a living being.

BACKGROUND ART

Stromal progenitors (SP) are cell populations that are capable of proliferation and differentiation, and also provide support for surrounding tissues and cells.

SP are rare cell elements located in the tissues of living beings, which are designed to perpetuate their function by turnover of damaged and/or senescent cells.

SP were initially found in high-turnover tissues, such as the hematopoietic and epithelial system, but can be found, although less frequently, in tissues and organs having little or no regenerative capacity, such as the central nervous system.

Originally, bone marrow studies started more than thirty years ago were able to identify certain SP, which will be referred to hereinafter as mesenchymal SP, which are capable of maintaining hemopoiesis and osteogenesis, thereby providing functional and structural support.

In vitro studies showed that these cells have a high proliferative potential, as well as differentiating capacities, in certain appropriate conditions, that is, the ability of converting into cell elements belonging to bone, cartilage, adipose, muscular and nervous tissue.

This knowledge related to the characteristics of bone marrow mesenchymal SP have extended the scope of research to introduce novel therapies in the so-called regenerative medicine.

Due to their differentiating potential, bone marrow mesenchymal SP have been studied for regeneration of injured tissues after trauma and acute and chronic degenerative events, such as cardiopathies. In oncology, they may be used to carry drugs having an antitumor action and also find application in autoimmune diseases, due to the production of immune response modulating molecules. Furthermore, due to their support function, they have been found to be useful as an aid in hemopoietic stem cell transplantation.

Some of these studies led to clinical applications of SP, in areas such as myocardial infarct, diabetes mellitus, autoimmune diseases, bone regeneration, burns, lipodystrophies and liver failure.

In all the above situations, and for an effective therapeutic application, a great number of SP needs to be infused or transplanted, i.e. in the order of various millions per kilogram weight of a patient.

This requires a prolonged expansion of SP outside of the donor, i.e. in vitro in culture flasks. This is required because of the poor presence of SP in the original bone marrow tissue, and may be a limitation.

Furthermore, the collection site (the bone marrow) may not be easily accessible and be damaged due to the presence of neoplastic cells or simultaneous pharmacological treatments.

Therefore, further SP collection sites have been considered, such as the periosteum, bone trabeculae, the skeletal muscle, the lung, the umbilical cord and particularly the subcutaneous adipose tissue (AT).

Concerning the AT, the main cell is the adipocyte, which is as large as about 100 μm and fulfills the main role of the AT, i.e. storing energy in the form of triglycerides introduced by diet.

Also in the AT, the SP are a pool of progenitors which replicate in response to appropriate hormone stimulation, thereby allowing a part of the progenies to differentiate into mature adipocytes, and also act as a support to vascular structures, whereby they are defined as stromal pericytes.

Adipose tissue is distributed in many anatomical districts into the body and divided into two fat types: white adipose tissue and brown adipose tissue.

Brown adipose tissue is scarcely traced in newborn and adults, in particular it can be found in rare anatomical regions, primarily into the interscapular region. White adipose tissue is the major component of adipose tissue of adults and is subdivided into two groups according to the resident anatomical district. Subcutaneous adipose tissue (SAT) makes up 80% of all body adipose tissue and is distributed mainly in the abdominal region, buttocks and flanks. Visceral white adipose tissue (VAT) represents about 10% of all body adipose tissue and is present in the omental and mesenteric regions (Lee M J et al, Adipose tissue heterogeneity: implication of depot differences in adipose tissue for obesity complicationsm Mol Aspects Med 2013; 34:1-11).

Another subcategory of visceral adipose tissue is the epicardial adipose tissue (EAT) which is the fat adjacent to the coronary arteries and myocardium and is actually considered to be brown adipose tissue because of its functional properties (Salgado-Somoza A. et al, Proteomic analysis of epicardial and subcutaneous adipose tissue reveals differences in proteins involved in oxidative stress, Am J Physiol Heart Circ Physiol 2010; 299:H202-H209).

AT mass in adult humans is a function of diet and life style and ranges from 2-3% the total weight in an athlete up to 60-70% in an obese individual.

The increased occurrence of obesity has increased AT availability, also due to an increase in cosmetic surgery for reducing subcutaneous adipose mass for aesthetic purposes or else. In these cases AT collection may presently be performed by liposuction.

As a result, AT is a potential source of SP, due to its abundance and accessibility.

Adipose depots of VAT and SAT, apparently morphologically similar, display instead numerous intrinsic differences in the adipocyte progenitor population, defined previously as stromal progenitors (SP). These two stromal progenitor populations have intrinsic differences in genomic expression profile, multidifferentiative capability, cellular response to both genetical factors and microenvironment (Macotela Y et al, Intrinsic differences in adipocyte precursor cells from different white fat depots, Diabetes 2012; 61:1691-1699; Peinado J R et al, The stromal vascular fraction of adipose tissue contributes to major differences between subcutaneous and visceral fat depots, Proteomics 2010; 10: 3356-3366).

SAT has a higher number of stromal progenitors comparing with VAT (Lee M J et al, supra) with a higher proliferative and differentiative capability versus VAT (Ong W K et al, Identification of specific cell-suface markers of adipose-derived stem cells from subcutaneous and visceral fat depots, Stem Cell Reports 2014;2:171-179).

Zuk P A et al, in the article "Human adipose tissue is a source of multipotent stem cells", published in Molecular Biology of The Cell (2002), started various studies to assess the analogy between SP of adipose and bone marrow origin.

These initial tests showed a number of analogies in terms of differentiation potential and antigen expression, and this preliminary data allowed the introduction of SP in many fields of regenerative medicine for cardiology and cosmetic medicine applications, particularly starting from patient-derived, i.e. autologous cells.

The present state of the art is limited by the large amounts of subcutaneous AT that must be collected to obtain an adequate number of SP. These volumes of collected fat are usually above 0.5 L and may be as large as 1 L. While these are large volumes in absolute terms, they have relatively little incidence on an obese or overweight patient, i.e. having a Body Mass Index (BMI) parameter exceeding 25. Those volumes cannot be obtained from low BMI individuals (having a BMI of less than 18.5), who may hardly have the required amount of autologous SP.

Therefore, this method in the prior art is only applicable to a limited number of patients.

Moreover, invasive surgical procedures are required, involving the hazards of any surgery, particularly fat embolism.

Further, AT collections always require a general anesthesia of the patient, with the related required care and potential hazards.

SUMMARY OF THE INVENTION

It is an object of the present invention to improve the prior art.

Another object of the invention is to provide a method of obtaining a population of cells that enables an extension of therapeutic applications of AT-derived SP to a greater number of individuals.

A further object of the invention is to provide a method of obtaining SP from a small AT mass, i.e. of the order of a few hundredths to thousandths of milliliter, which is present and easily collectable in all types of patients, even in very thin individuals (with a BMI of less than 18.5).

Yet another object of the invention is to collect sufficient amounts of SP from the AT under local anesthesia.

In one aspect, the invention relates to a method of obtaining a population of SP cells as described hereinafter.

Some of the advantages provided by the present invention include:

collecting an adequate number of SP from a very small volume of AT in patients, possibly patients having a BMI of less than 18.5;

obtaining considerable amounts of cells from very small amounts of tissue collected from a patient;

obtaining the small amounts of collected tissue through minimally invasive surgery, under local anesthesia, with considerably reduced hazard, discomfort and pain for the patient;

using small amounts of AT to isolate a population of SP which maintains the properties of its progenitors, i.e. immunogen characteristics and differentiation capacities; and obtaining progenitor cells from patients for further transplantation to regenerate damaged tissues.

BRIEF DESCRIPTION OF THE DRAWINGS

Additional features and advantages of the invention will be more readily apparent from a detailed description of non-exclusive embodiments of a method of obtaining a population of cells, particularly SP cells from AT, which are exemplarily illustrated in the enclosed drawings, where:

FIG. 3a is a view of the adipose mass, FIG. 3b is a view of the cells adhered to the plastic of a culture flask or container and defined as pre-adipocytes (zone 1);

DETAILED DESCRIPTION OF EMBODIMENTS OF THE INVENTION

A method is provided for effectively obtaining a population of stromal progenitor cells. In one embodiment, a method according to the invention includes the steps of extracting a first quantity $q_1$ of subcutaneous white adipose tissue from a living individual and isolating adipose stromal progenitor cells from the first quantity $q_1$; putting the first quantity $q_1$ inside a culture media together with a second quantity $q_2$ of a buffer to digest the first quantity and to obtain, after digestion, an expansion of the adipose stromal progenitor cells according the following examples.

The cellular population obtained with the above method is represented by stromal progenitors derived from subcutaneous adipose tissue. These cells can be obtained in useful quantities from a reduced amount of adipose tissue using a method according to the invention, typically from patients with low body mass index (BMI), and maintain their high differentiative capability as necessary for applications in regenerative medicine.

EXAMPLE 1

Production of a Population with Desired Characteristics

An AT sample was collected from the subcutaneous facial area of a healthy 46-year old female donor by Coleman liposuction. Alternate methods may be used for collection.

The AT fragments were washed three times with a saline solution known as Dulbecco-phosphate buffer solution (D-PBS) added with antibiotic (1 U/mL penicillin, 1 mg/mL streptomycin and 2.5 mg/mL amphotericin B), for an overall time of 15 minutes.

The last washing step, which was designed to yield a sample with no liquid component, was carried out using a filter (100 μm cell strainer).

Figure 1:
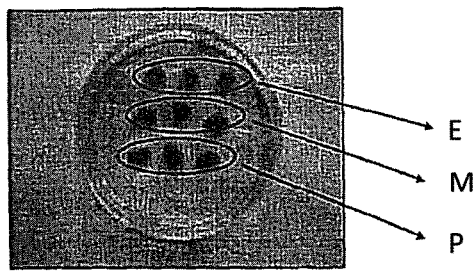
FIG. 1 is a view of the lipo-suctioned sample divided into nine parts, each having a volume of about 0.020-0.025 mL and undergoing three different procedures in triplicate, namely, the parts designated as sample E underwent an enzyme digestion process, the three parts designated as sample M underwent a mechanical digestion process, and the three parts designated as sample P were cultivated.

The AT fragments were transferred into a sterile container (Petri dish) and divided into nine parts, each having a volume of about 0.025 mL. The latter, as shown in FIG. 1, underwent three different procedures in triplicate: three parts (sample E) underwent the same enzyme digestion process, three parts (sample M) underwent the same mechanical digestion process and finally, the last three parts (sample P) were all cultivated.

Sample E was digested using the enzyme solution, consisting of the enzyme buffer added with the enzyme mixture, and at the same time sample M was mechanically digested, i.e. using the enzyme buffer only and no enzyme mixture, and finally sample P was cultivated without processing.

Samples E and M were fragmented using eye scissors. Sample E was incubated at 37° C. with the enzyme solution, and sample M with the enzyme buffer, in a ratio of 0.004 mL AT per each mL of each solution.

The enzyme buffer is a medium generally known as Dulbecco's Modified Eagle Medium (DMEM), added with 1 U/mL penicillin, 1 mg/mL streptomycin, 1 mM sodium pyruvate, non-essential amino acids (a solution composed of: L-alanin (0.89 mg/dL); L-asparagin $H_2O$ (1.5 mg/dL); L-aspartic acid (1.33 mg/dL); L-glutamic Acid (1.47 mg/dL); glycin (0.75 mg/dL); L-prolin (1.15 mg/dL); L-serin (1.05 mg/dL).

The enzyme mixture, e.g. a mixture known as "COLLAGENASE P", sold by Roche, contains clostripain in a concentration of 2.8 U/mg lyophilizate, protease (Azocoll) in a concentration of 160 U/mg and tripsin (BAEE) in a concentration of 0.23 U/mg.

Samples E and M were transferred into one or more 50 ml cylindrical containers known as Falcon.

Figure 2A:
FIG. 2a is a view of the skeleton of adipose tissue in a supernatant after enzyme digestion, obtained using an inverted microscope (at x-100 magnification)

The quantity of each sample in each container was about 30 ml, and the AT samples were stirred at 37° C. for 120 minutes, i.e. the ideal conditions for enzyme activity. Oscillation was longitudinally directed (75 oscillations/minute) in the direction of the longitudinal axis of the container. At the end of the incubation time, the samples were centrifuged at 1,500 rpm for 10 minutes, thereby yielding a supernatant, to be discarded, and a pellet composed of all AT cell elements. Referring to FIG. 2a, observation of sample E with an optical microscope shows the presence of the skeleton of adipose tissue in the supernatant, confirming that such tissue was effectively digested by collagenase.

The pellet was washed two more times after filtration using a 100 μm cell strainer to remove mature adipocytes.

Figure 2B:
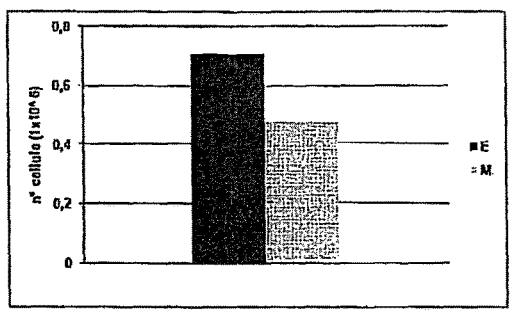
FIG. 2b is a diagram showing the number of cells (in millions) obtained after digestion of samples E and M.

Once the above process was completed, cell counting was performed with a cell survival test using 0.4% Trypan Blue staining. 701,000 cells and 482,000 cells were obtained on average for samples E and M respectively (FIG. 2b).

These cells were seeded with a density of 10,000/cm² in cell culture containers (flasks) with a Quantum 333 medium added with 1 U/mL penicillin and 1 mg/mL streptomycin.

Figures 3A, 3B, 3C, 3D:
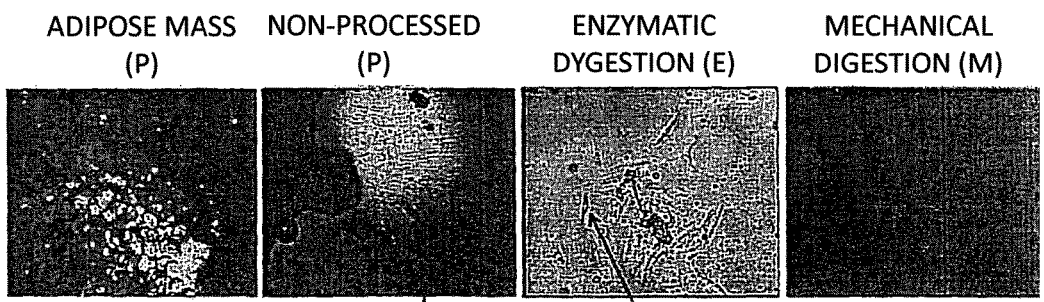
FIGS. 3a and 3b are two images of an in vitro culture of sample P, obtained at zero days and seven days respectively, more particularly.
FIG. 3c is an image of the 10-days in vitro culture of a sample E, which shows the presence of both adherent pre-adipocytes and SP isolated from adipose tissue.
FIG. 3d is an image obtained using an inverted microscope (at x-100 magnification) of the 10-days in vitro culture of a sample M where it can be noted that the simple culture process is not effective in SP isolation, as no cells are shown to adhere to the culture flask or container.

FIGS. 3a and 3b show the in vitro culture of sample P at 0 days and 7 days respectively.

The unprocessed 0-day sample exhibits the adipocyte-rich adipose mass (FIG. 3a), while FIG. 3b shows, at 7 days, cell elements adhering to the plastic and arranged around the adipose mass.

These cell elements have an elongate shape and are characterized by the presence of small intra-cytoplasmic lipid vacuoles, and hence are called pre-adipocytes (zone A in FIG. 3b).

After 15 days, in spite of the great number of cells that were isolated initially, the culture of sample P showed a limited growth, no in vitro expansion being thus observed.

Conversely, after 10 days from start of culture, sample E was found to contain about 50% pre-adipocytes and as many fibroblastoid elements in the flask (zone 1 of FIG. 3c).

Finally, FIG. 3d shows sample M. No cell population could be isolated here, because no cells adhered to the culture flask.

The cultures so prepared were continued in the incubator at a controlled atmosphere (37° C., 5% $CO_2$) and the medium was replaced every 2-3 days to full flask growth, which was achieved by sample E only.

Later steps involved trypsinization with a trypsin-EDTA solution (0.05%-0.02%) and reseeding in new flasks with a density of 5000 cells/cm².

Figure 4:
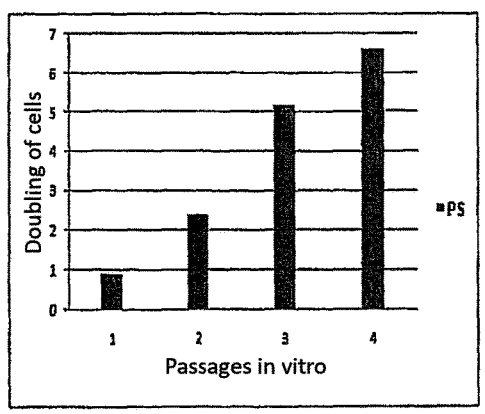
FIG. 4 is a diagram that shows the growth of sample E, in which SP cell doubling is shown in the first four culture passages.

After culture passage four, 50×10⁶ cells were obtained in sample E, whereas no growth was observed in the other groups. Cell doubling was calculated with the formula $\log(N_1/N_2)/\log 2$, where $N_1$ e $N_2$ are the cell count at the ith passage and at the i+1th passage (FIG. 4). In vitro growth of SP was found to follow an exponential curve.

Figure 5A:
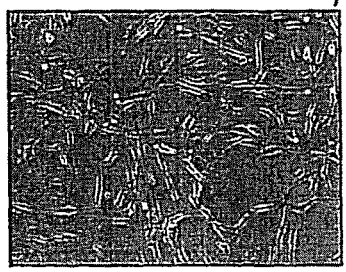
FIG. 5a is an image of the SP of sample E at culture passage four.

Furthermore, the SP so isolated (FIG. 5a) maintained a typically fibroblastoid phenotype in the culture, and no longer showed the typical intracytoplasmic vacuoles of pre-adipocytes.

Figure 5B:
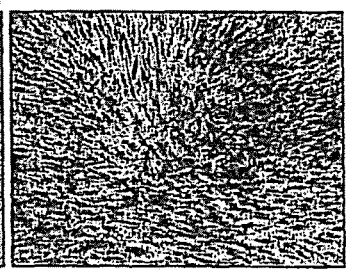
FIG. 5b is an image of SP showing negativity for staining of typically intra-cytoplasmic fat droplets, known as Oil-Red O.
Figure 5C:
FIG. 5c is an image of the pre-adipocytes isolated from sample P, showing positivity for Oil-Red-O staining.

Hence, as shown in FIG. 5b, the SP were found to be negative for "Oil Red O" staining, which stains intracellular granules. When comparing the SP with the pre-adipocytes isolated from sample P (FIG. 5c), the SP were found to have lost the typical intracytoplasmic lipid vacuoles of pre-adipocytes, and to maintain a fibroblastoid phenotype. This shows conversion of pre-adipocytes to a more undifferentiated stage.

The SP so obtained in the process were used for later analysis (immunophenotype and differentiation assays), which confirmed the desired characteristics of the population obtained with a method according to the invention.

EXAMPLE 2

Immunophenotyping Evaluation

Figure 6A:
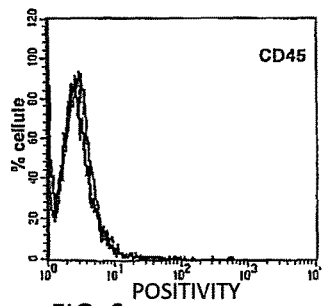
FIG. 6a is a diagram showing the expression of the CD45 antigen.
Figure 6B:
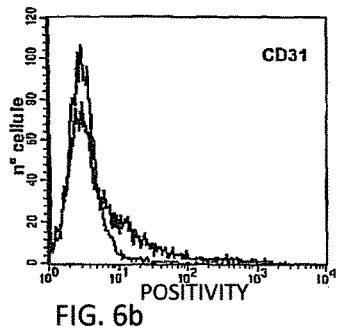
FIG. 6b is a diagram showing the expression of the CD31 antigen.

A check was first made for the presence of any contaminating population, such as endothelial cells and immune system cells, by searching for their respective CD31 and CD45 markers. The SP were found to be negative for CD45 (FIG. 6a) and very weakly positive for CD31 (FIG. 6b).

Figure 6C:
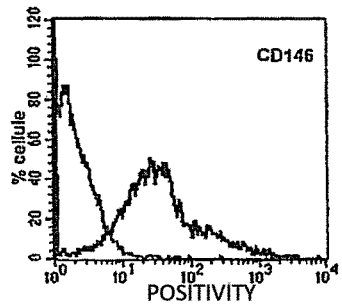
FIG. 6c is a diagram showing the expression of the CD146 pericyte antigen.
Figure 6D:
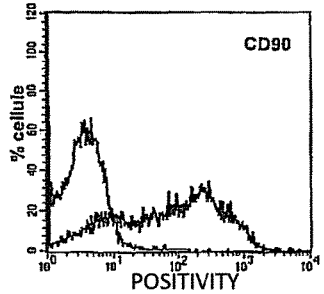
FIG. 6d is a diagram showing the expression of the CD90 antigen.
Figure 6E:
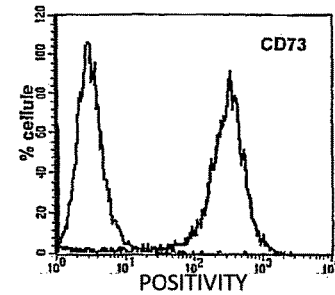
FIG. 6e is a diagram showing the expression of the CD73 antigen.
Figure 6F:
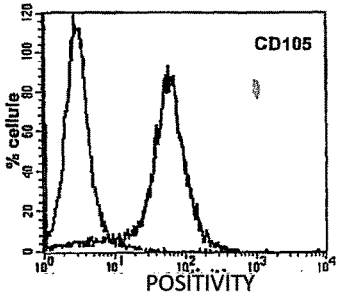
FIG. 6f is a diagram showing the expression of the CD105 antigen.

At the same time, the SP were found to be positive for progenitor antigens, such as CD90 (FIG. 6d), CD105 (FIG. 6f) and CD73 (FIG. 6e) and to a lesser extent for CD146 (FIG. 6c) as a typical stromal pericyte marker.

EXAMPLE 3

Differentiation Assays

Osteogenic, adipogenic and chondrogenic and differentiation of the SP were performed after phenotyping, at passage 4.

Osteogenic Differentiation.

The cells were seeded at a density of 10,000 cells/cm$^2$. After full growth (typically after 2-4 days), they were induced osteogenic differentiation, with one sample being preserved as control.

Bone induction was obtained using an appropriate medium, composed of: basal medium (DMEM with 10% fetal calf serum—FCS) dexamethasone, L-ascorbic-2-phosphate acid and β-glycerophosphate.

Such basal medium was maintained for one week, and replaced every 2-3 days. On the seventh day, or day 7, bone morphogenetic protein-2 was added to the medium. The cells were maintained with the differentiating medium for seven more days, and such medium was replaced every two-three days.

On the fourteenth day, the differentiation result was assessed by histological assay (Alizarin Red staining). In this assay, the cells in the flasks are briefly washed in a Tris-HCl and NaCl solution (3-5 mL/flask), fixed with 100% methanol at 4° C. for 30 minutes and briefly washed twice in deionized water. Then, the cells are left in contact with a (0.5%) Alizarin Red solution at pH 4.0-4.2 for five minutes and briefly washed.

Figure 7A:
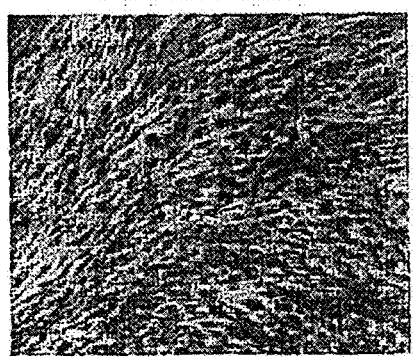
FIG. 7a shows an image obtained using an inverted microscope of non osteogenically induced SP, negative for Alizarin RED staining.
Figure 7B:
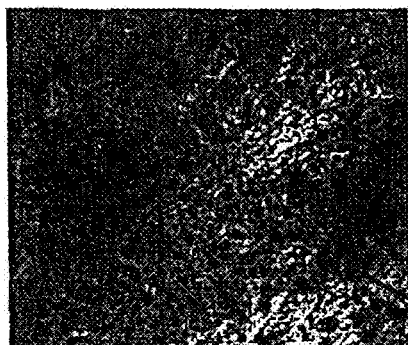
FIG. 7b shows a x-100 magnified image of osteogenically induced SP, i.e. positive for Alizarin Red staining.

Appropriately induced cells have typical properties of bone tissue osteoblasts, such as production of bone matrix deposits, as observed in zone 1 of FIG. 7b, which are not present in the non-induced control, as shown in FIG. 7a.

Adipogenic Differentiation.

The cells were seeded at a density of 10,000 cells/cm$^2$ in their culture medium. Once full growth was achieved (generally after two-four days), adipogenic differentiation was induced, using one culture as a control.

The only medium for adipogenic differentiation is DMEM added with horse serum and rabbit serum, dexamethasone, insulin, isobutyl methyl xanthine (IBMX), indomethacin and penicillin/streptomycin.

The cells were maintained under differentiating conditions for 10 days, and the medium was replaced every two-three days. On the tenth day, the optical microscope revealed the appearance of characteristic cell clusters containing lipid vacuoles.

These vacuoles were more apparent by Oil Red O staining. The cells were washed in a saline solution and fixed with 40% formalin fumes for ten minutes.

Then they were washed in ddH2O for two minutes, followed by staining with an Oil Red O solution (2%) for five minutes. In order to highlight nuclear and cytoplasmic structures, the cells were treated with hematoxylin as a counterstain (30"-1'). Finally, they were washed in water for five minutes.

Figure 7C:
FIG. 7c shows a x-100 magnified image of non-adipogenically induced SP, i.e. negative for Oil-RED-O staining.
Figure 7D:
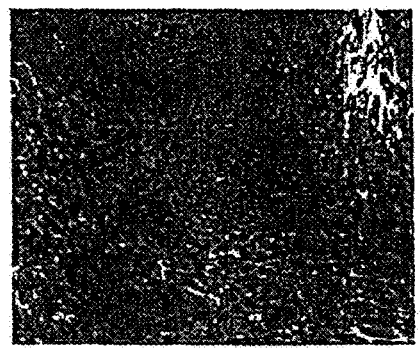
FIG. 7d shows a x-100 magnified image of adipogenically induced SP, i.e. positive for Oil-Red-O staining.

The cells were thus differentiated into adipocytes, as shown by the presence of lipid vacuoles. Such presence is further confirmed by their positivity for "Oil Red O" staining (see FIG. 7d) and further validated by the negativity of the control, which only exhibits the purple counterstain of hematoxylin (see FIG. 7c).

Chondrogenic Differentiation.

The cells obtained from the adherent phase are divided into 15 mL conical tubes (2×105 cells/mL) with DMEM high glucose supplemented with BMP-6, TGF-β3, dexamethasone, L-ascorbic-2-phosphate acid, sodium pyruvate, proline, glutamine and penicillin/streptomycin.

The cells were centrifuged to the bottom of 15 mL conical tubes and cultivated, with the medium changed every two days.

On the twenty-first differentiation day, the pellets were collected, fixed in formalin and included in paraffin.

Serial sections of induced and non-induced samples were then stained with an Alcian Blue solution. This is a basic water-soluble copper phthalocyanin stain which stains the acidic groups of hyaluronic acid produced by chondro-differentiated cells.

Figure 7E:
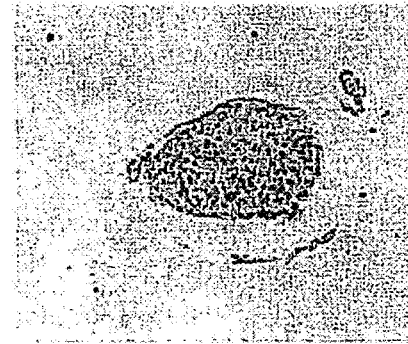
FIG. 7e shows a x-100 magnified image of non-chondrogenically induced SP, i.e. negative for Alcian Blue staining.
Figure 7F:
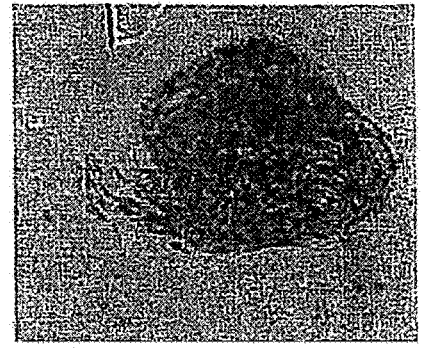
FIG. 7f shows a x-100 magnified image of chondrogenically induced SP, i.e. positive for Alcian Blue staining.

The induced Alcian Blue stained sample assumes a stronger stain (see FIG. 7f) as compared with the non-induced control (see FIG. 7e). Hyaluronic acid is stained, and its production causes a volume increase of the induced sample, when compared with the non-induced sample.

Therefore, the differentiation assays, in combination with immunophenotyping, confirmed the multipotential progenitor characteristics of isolated cells, even when using small amounts of AT.

EXAMPLE 4

Two enzymatic digestions were performed starting from two different biological samples of subcutaneous adipose tissue.

Biological Sample 1:

Isolation of stromal progenitors from subcutaneous adipose tissue was achieved by performing two sequential enzymatic digestion starting from a quantity of adipose tissue of 24.7 mg for each process. These 24.7 mg of adipose tissue were digested using a volume of 15 ml of enzymatic solution, corresponding to a ratio of 1.6 mg for each ml of enzymatic solution.

The enzymatic digestion was extended for 90 minutes at 37° C. in agitation.

After the two enzymatic digestion, 400.000 cells and 211.100 cells were obtained respectively.

The cells were seeded and kept in culture. After 11 days, rare large and senescent cells were visible, adhered to the plastic support of the culture.

Figure 8:
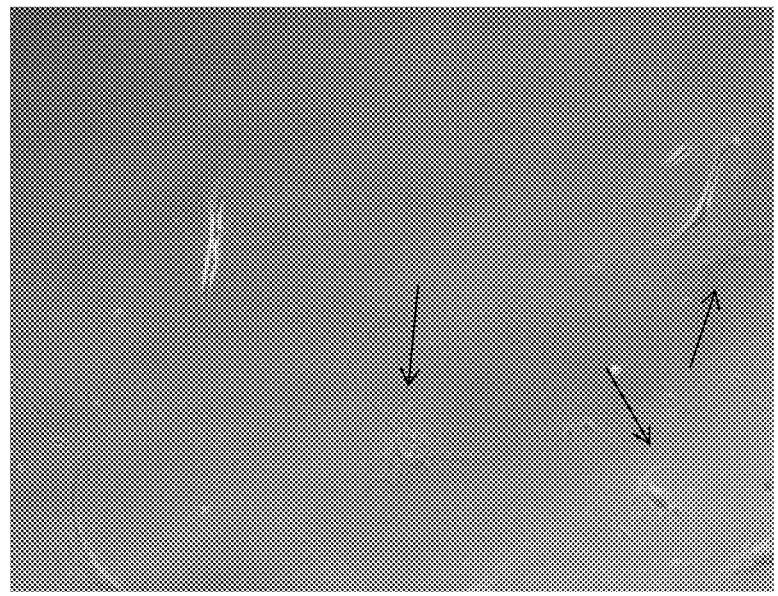
FIG. 8. shows a x-100 magnified image of a cell culture after 12 days of insulation.

FIG. 8 shows the image of the cell culture (×-100 magnification) at 12 days of culture post-isolation. That image shows rare dispersed cells characterized by marked cytoplasmic extensions (arrows), a peculiarity of suffering and senescent cells (as reported by: Zaim M et al, Donor age and long-term culture affect differentiation and proliferation of human bone marrow mesenchymal stem cells, Ann Hematol. 2012 Aug;91(8):1175-86; Stolzing A et al, Age-related changes in human bone marrow-derived mesenchymal stem cells: consequences for cell therapies, Mech Ageing Dev. 2008 Mar;129(3):163-73).

Both isolated samples were eliminated because of the unsuccessful of enzymatic digestion.

Biological Sample 2:

Isolation of stromal progenitors was obtained from subcutaneous adipose tissue performing two sequential enzymatic digestion starting from a quantity of adipose tissue of 118.9 mg and 74.4 mg respectively. These quantities of adipose tissue were digested using a volume of 40 mL and 30 mL of enzymatic solution respectively, corresponding to a ratio of 2.5 mg of each ml of enzymatic solution. The enzymatic digestion was protracted for 60 minutes at 37° C. in agitation. After the two enzymatic digestion, 2,466,600 cells were obtained starting from 118.9 mg and 3,466,700 cells starting from 74.4 mg. The cells were seeded and kept in culture. After 8 days rare large and senescent were visible adhered to the plastic support of the culture.

Figure 9:
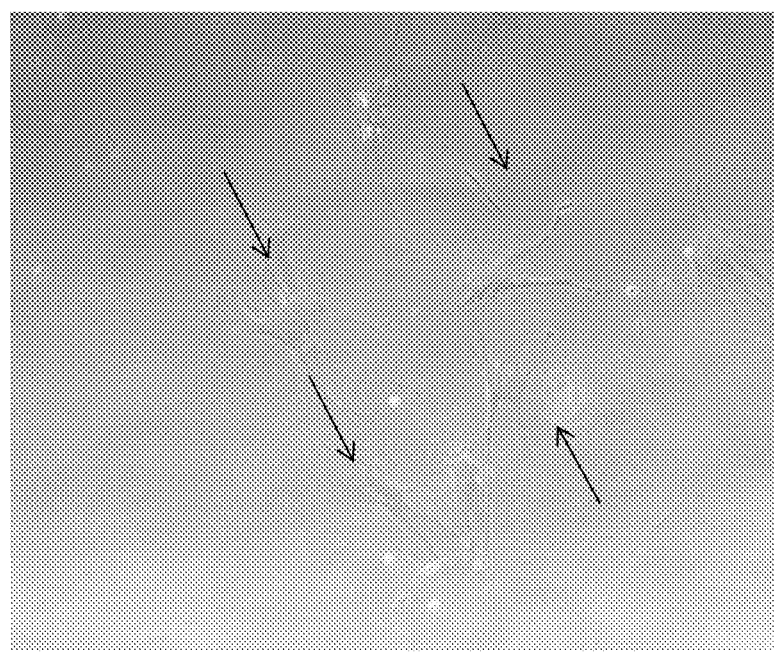
FIG. 9 shows a ×-100 magnified image of a cell culture after 8 days of insulation.
Figure 8A:
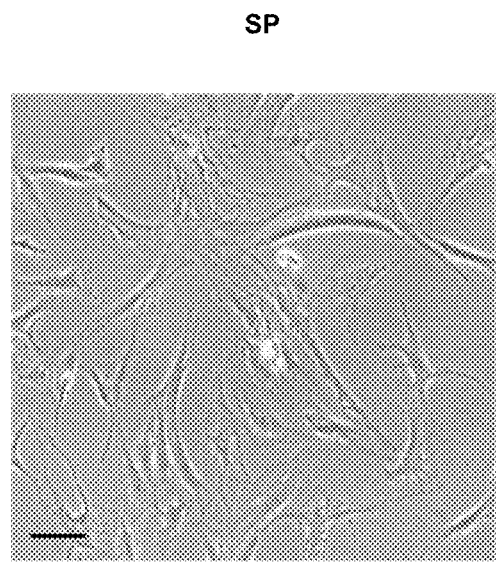
FIG. 8a shows an image of SP as in Example 5 obtained using inverted microscope at x-100 magnified image.
Figure 8B:
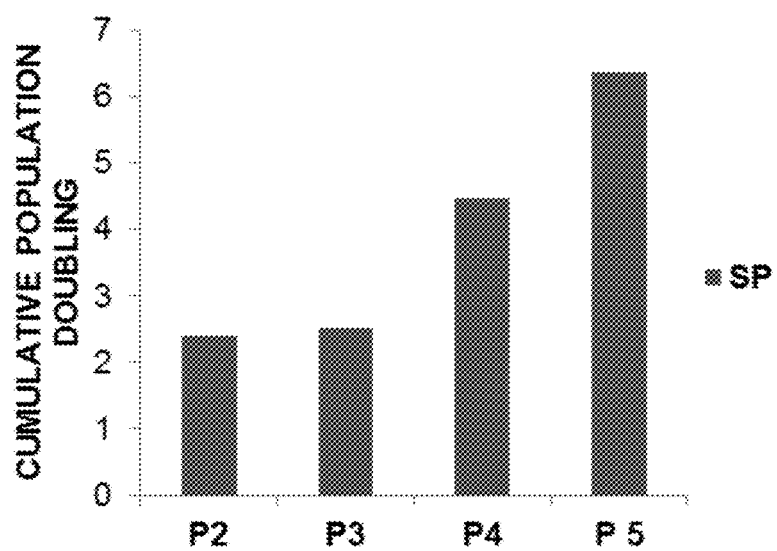
FIG. 8b shows a diagram illustrating the growth of SP as in Example 5, showing in detail the doubling of cells for the first five passages.

FIG. 9 shows the image of the cell culture (×-100 magnification) at eight days of culture post-isolation as an example. This image displays rare dispersed cells characterized by marked cytoplasmic extensions (arrows), a peculiarity of suffering and senescent cells (as reported by: Zaim M et al, supra; Stolzing A et al, supra).

Both isolated samples were eliminated because of the unsuccessful enzymatic digestion.

Therefore, the invention has been found to fulfill the intended objects.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become apparent to those skilled in the art and the scope of the present invention is limited only by the appended claims.

The invention claimed is:

1. A method of obtaining a population of stromal progenitor cells comprising the steps of:
    collecting a first quantity $q_1$ of subcutaneous adipose tissue containing white adipose cells from a living being;
    digesting the first quantity $q_1$ with a second quantity $q_2$ of enzymatic solution comprising collagenase to obtain a population of free cells;
    seeding the population of free cells into a culture medium; and
    obtaining stromal progenitors cells from the seeded cells, wherein $q_1$ is between 0.004 ml and 0.036 ml and $q_2$ is between 0.9 ml and 1.1 ml, and
    wherein $q_1$ and $q_2$ can be proportionally scaled up or down.

2. The method according to claim 1, wherein said enzymatic solution comprises:
    Dulbecco's Modified Eagle Medium (DMEM);
    penicillin (1 U/ml) & streptomycin (1 mg/ml);
    sodium pyruvate (1 mM); and
    non-essential amino acids comprising: L-alanine (0.89 mg/dl); L-asparagine H2O (1.5 mg/dl); L-aspartic Acid (1.33 mg/dl); L-glutamic Acid (1.47 mg/dl); glycine (0.75 mg/dl); L-proline (1.15 mg/dl); and L-serine (1.05 mg/dl).

3. The method according to claim 1, wherein said enzymatic solution comprises:
    class I and II collagenase mixture; or
    class I and II collagenase mixture with an enzymatic concentration between 1.74 and 1.78 U/ml of said enzymatic solution.

4. The method according to claim 1, wherein said enzymatic solution comprises:
    clostripain; and
    trypsin.

5. The method according to claim 1, wherein the step of digesting comprises joining said first and second quantities $q_1$ and $q_2$ together, and, between the steps of collecting and seeding, shaking said first and second quantities $q_1$ and $q_2$ with a shaking device for a time between 20 minutes and 120 minutes at a predetermined temperature.

6. The method according to claim 5, wherein said predetermined temperature is between 36° C. and 38° C.

7. The method according to claim 5, wherein the step of shaking comprises swinging said shaking device in a first swinging direction with a first number of swings per minute and in a second swinging direction different from said first swinging direction and with a second number of swings per minute.

8. The method according to claim 7, wherein said shaking device comprises a tubular container.

9. The method according to claim 8, wherein said shaking device is adapted to move said tubular container in a direction of a longitudinal axis of said tubular container.

10. The method according to claim 7, wherein said first number is between 70 and 80 swings per minute and said second number is between 6 and 100 swings per minute.

11. The method according to claim 1, wherein said stromal progenitor cells comprise mesenchymal stromal cells and stromal pericytes.

12. The method according to claim 1, wherein seeding the population of free cells into a culture medium further comprises the step of expanding the population of free cells in the culture medium, wherein the culture medium comprises a synthetic basal medium with an antibiotic added therein.

* * * * *